United States Patent
Zlotkin

(10) Patent No.: US 10,508,136 B2
(45) Date of Patent: *Dec. 17, 2019

(54) PEPTIDES AND COMPOSITIONS FOR PREVENTION OF CELL ADHESION AND METHODS OF USING SAME

(71) Applicant: TEL HASHOMER MEDICAL RESEARCH, INFRASTRUCTURE AND SERVICES LTD., Tel Hashomer (IL)

(72) Inventor: Amir Zlotkin, Tel Hashomer (IL)

(73) Assignee: TEL HASHOMER MEDICAL RESEARCH, INFRASTRUCTURE AND SERVICES LTD., Tel Hashomer (IL)

(*) Notice: Subject to any disclaimer, the term of this patent is extended or adjusted under 35 U.S.C. 154(b) by 0 days.

This patent is subject to a terminal disclaimer.

(21) Appl. No.: 15/673,632

(22) Filed: Aug. 10, 2017

(65) Prior Publication Data

US 2018/0186845 A1 Jul. 5, 2018

Related U.S. Application Data

(60) Continuation of application No. 14/725,962, filed on May 29, 2015, now Pat. No. 9,732,124, which is a division of application No. 14/016,480, filed on Sep. 3, 2013, now Pat. No. 9,045,550, which is a division of application No. 13/142,358, filed as application No. PCT/IB2009/007896 on Dec. 28, 2009, now Pat. No. 8,552,147.

(60) Provisional application No. 61/193,821, filed on Dec. 29, 2008.

(51) Int. Cl.
| | | |
|---|---|---|
| C07K 14/435 | (2006.01) | |
| C07K 7/06 | (2006.01) | |
| C07K 7/08 | (2006.01) | |
| C02F 1/44 | (2006.01) | |
| C02F 1/50 | (2006.01) | |

(52) U.S. Cl.
CPC ............ C07K 14/435 (2013.01); C02F 1/441 (2013.01); C02F 1/50 (2013.01); C07K 7/06 (2013.01); C07K 7/08 (2013.01); C07K 14/43595 (2013.01); *C02F 2303/04* (2013.01); *C02F 2303/20* (2013.01)

(58) Field of Classification Search
CPC .. C07K 14/435; C07K 14/43595; C07K 7/06; C07K 7/08; C02F 1/441; C02F 1/50; C02F 2303/04; C02F 2303/20
See application file for complete search history.

(56) References Cited

U.S. PATENT DOCUMENTS

| | | | |
|---|---|---|---|
| 7,189,351 B2 | 3/2007 | Levin et al. | |
| 8,552,147 B2 | 10/2013 | Zlotkin | |
| 9,045,550 B2 | 6/2015 | Zlotkin | |
| 2002/0143149 A1* | 10/2002 | Duckworth | C07K 14/705 530/350 |
| 2002/0146692 A1 | 10/2002 | Yamazaki et al. | |
| 2003/0113798 A1 | 6/2003 | Burmer et al. | |
| 2006/0057582 A1 | 3/2006 | Rosen et al. | |

FOREIGN PATENT DOCUMENTS

| | | |
|---|---|---|
| AU | 2009334452 B2 | 7/2010 |
| EP | 2 376 528 B1 | 10/2011 |
| JP | 5758302 B2 | 8/2015 |
| WO | WO-02/061087 A2 | 8/2002 |
| WO | WO-03/006048 A1 | 1/2003 |
| WO | WO-2005/121778 A2 | 12/2005 |
| WO | WO-2006/006172 | 1/2006 |
| WO | WO-2009/037714 A2 | 3/2009 |
| WO | WO-2010/035107 A2 | 4/2010 |
| WO | WO-2010/078842 A1 | 7/2010 |

OTHER PUBLICATIONS

Neumann et al, Functional Immobilization of a Ligand-Activated G-Protein-Coupled Receptor, ChemBioChem, 2002, 3, pp. 993-998.*

Adessi et al., Converting a peptide into a Drug: Strategies to Improve Stability and Bioavailability, Current Medicinal Chemistry, 2002, pp. 963-978.

Balaban N. et al: "Use of the Quorum-Sensing Inhibitor RNAIII-Inhibiting Peptide to Prevent Biofilm Formation In Vivo by Drug-Resistant Staphylococcus epidermidis" Journal of Infectious Diseases, University of Chicago Press, Chicago, IL. LNKD.DOI:10.1086/345979, vol. 187, No. 4, Feb. 7, 2003 (Feb. 7, 2003), pp. 625-630.

CK1/CK1 protein kinase—*Nematocida* sp.1, from http://www.ncbi.nlm.nih.gov/protein/EHY66175.1, pp. 1-2, accessed Apr. 14, 2014.

(Continued)

*Primary Examiner* — Karlheinz R. Skowronek
*Assistant Examiner* — Li N Komatsu
(74) *Attorney, Agent, or Firm* — Foley & Lardner LLP

(57) ABSTRACT

Compositions comprising an isolated peptide, which may for example optionally comprise a sequence selected from the group consisting of FDYDWY (SEQ ID NO: 2), SFSQNKSVHSFDYDWYNVSDQADLKN (SEQ ID NO: 3) or CSFSQNKSVHSFDYDWYNVSDQADLKNC (SEQ ID NO: 1), or any cyclized version thereof, and methods of using same, including for treatment of or prevention of formation of microbial biofilms and against adhesion of a cell to a surface.

31 Claims, 4 Drawing Sheets
Specification includes a Sequence Listing.

(56) References Cited

OTHER PUBLICATIONS

The International Search Report received in the corresponding International Patent Application No. PCT/IB2009/007896, dated May 31, 2010.
Hall-Stoodley, L., et al.; "Bacterial Biofilms: From the Natural Environment to Infectious Diseases"; Natural Reviews/Microbiology; 2:95-108 (Feb. 2004).
Japanese Patent Office action issued in application 2014-256935 dated Jan. 13, 2016; pp. 1-5 (with English translation).
Joo, Cyclic Peptides as Therapeutic Agents and Biochemical Tools, Biomol Ther, 2012, 20, pp. 19-26.
Klueh et al, Efficacy of Silver-Coated Fabric to Prevent Bacterial Colonization and Subsequent Device-Based Biofilm Formation, Inc. J Biomed Mater Res (Appl Biomater), 2000, 53, pp. 621-631.
Office Action dated Oct. 2, 2013 in Japan Appln. No. 2011-542917, with translation.
Sauer, K., et al.; "Characterization of Nutrient-Induced Dispersion in Pseudomonas aeruginosa PAO1 Biofilm"; Journal of Bacteriology, 186(21): 7312-7326 (2004).
Sauer, K., et al.; "Pseudomonas aeruginosa Displays Multiple Phenotypes during Development as a Biofilm"; Journal of Bacteriology, 184(4): 1140-1154 (2002).
Sher, et al.; "Toxic polypeptides of the hydra—a bioinformatics approach to cnidarian allomones"; Toxicon 45(2005): 865-879; Mar. 2005.
Silvestry-Rodriguez, Silver as a Residual Disinfectant to Prevent Biofilm Formation in Water Distribution Systems, Applied and Environmental Microbiology, 2008, 74, pp. 1639-1641.
Spangenberg C et al.: "Cloning and Characterization of a Novel Gene (TM7SF1) Encoding a Putative Seven-Pass Transmembrane Protein That is Upregulated During Kidney Development" Genomics, Academic Press, San Diego, U.S. LNKD-DO1: 10.1006/GENO, 1997.5170, vol. 48, No. 2, Mar. 1, 1998 (Mar. 1, 1998), pp. 178-185.

* cited by examiner

PEPTIDES AND COMPOSITIONS FOR PREVENTION OF CELL ADHESION AND METHODS OF USING SAME

CROSS-REFERENCE TO RELATED PATENT APPLICATIONS

This application is a Continuation of U.S. patent application Ser. No. 14/725,962, filed on May 29, 2015, now U.S. Pat. No. 9,732,124, which is a Continuation of U.S. patent application Ser. No. 14/016,480, filed on Sep. 3, 2013, now U.S. Pat. No. 9,045,550, which is a Divisional of U.S. patent application Ser. No. 13/142,358, filed on Jul. 12, 2011, now U.S. Pat. No. 8,552,147, which is the U.S. National Phase of PCT/IB2009/007896, filed Dec. 28, 2009, which claims priority from U.S. Provisional Application No. 61/193,821, filed Dec. 29, 2008, which are incorporated herein by reference in entirety.

SEQUENCE LISTING

The instant application contains a Sequence Listing which has been submitted in ASCII format via EFS-Web and is hereby incorporated by reference in its entirety. Said ASCII copy, created on Sep. 22, 2011, is named 09543201.txt and is 8,230 bytes in size.

FIELD OF THE INVENTION

The present invention relates to isolated peptides and their use in prevention of cell adhesion.

BACKGROUND OF THE INVENTION

Microorganisms can live and proliferate as individual cells swimming freely in the environment (as plankton), or they can grow as highly organized, multicellular communities encased in a self-produced polymeric matrix in close association with surfaces and interfaces. The latter microbial lifestyle is referred to as biofilms. Biofilm formation represents an ancient, protected mode of growth that allows microbial survival in hostile environments and allows microorganisms to disperse and colonize new niches [Hall-Stoodley et al., Nat Rev Microbiol. (2004) 2(2):95-108].

The composition of biofilms is complex and variable among different microbial species and even within the same species under different environmental conditions. Nonetheless, biofilm formation represents the normal lifestyle of microorganism in the environment and all microbes can make biofilms. Previous studies revealed that bacterial biofilm formation progresses through multiple developmental stages differing in protein profiles [Sauer et al., J Bacteriol. (2002) 184(4):1140-54], beginning with attachment to surface, followed by the immigration and division to form microcolonies and finally maturation involving expression of matrix polymers. Bacteria within each biofilm stage display phenotypes and possess properties that are markedly different from those of the same group growing planktonically [Sauer et al., J Bacteriol. (2004) 186(21):7312-26].

Biofilms are a major cause of systemic infections (e.g. nosocomial infections) in humans. In the body, biofilms can be associated with tissues (e.g., inner ears, teeth, gums, lungs, heart valves and the urogenital tract). An estimated 65% of bacterial infections in humans are biofilm in nature. Additionally, after forming biofilms, microorganisms tend to change their characteristics, sometimes drastically, such that doses of antibiotics which normally kill the organisms in suspended cultures are completely ineffective against the same microorganisms when the organisms are in attached or conglomerate biofilm form (U.S. Pat. No. 7,189,351).

One of the principal concerns with respect to products that are introduced into the body (e.g., contact lenses, central venous catheters, mechanical heart valves and pacemakers) or provide a pathway into the body is microbial infection and invariably biofilm formation. As these infections are difficult to treat with antibiotics, removal of the device is often necessitated, which is traumatic to the patient and increases the medical cost. Accordingly, for such medical apparatuses, the art has long sought means and methods of rendering those medical apparatuses and devices antimicrobial.

PCT Application No. WO 06/006172 discloses the use of anti-amyloid agents, such as aromatic compounds, for inhibiting formation or disintegrating a pre existing biofilm. The application discloses that compounds preventing amyloid fibril formation in Alzheimers can act against fibril formation in biofilms, and concludes that amino acids having an aromatic arm are effective against biofilms. However, the analysis was limited to full length sequences.

SUMMARY OF THE INVENTION

The present invention provides natural or synthetic peptides isolated from animals, including mammals and non-mammals, that interfere with biofilm formation at its initial stages, in a wide range of microorganisms.

All peptides described herein show activity that is exclusively directed to the prevention of microbial substrate adhesion and the derived biofilm formation. It is devoid of the commonly observed lethal bactericidal activity, revealed by the antibiotic peptides and secondary metabolites, which provides a strong selective pressure for rapid natural selection by the intensive microbial "biotic potential." On the other hand a wide range inhibition of microbial colonization antagonizes a fundamental mechanism of bacterial survival. Therefore an adaptive modification of such mechanism has a low likelihood due to its vitality.

Sher et al. (Toxicon 45: 865-879, 2005) identified putative biologically active proteins and polypeptides expressed by hydrae which could be components of its allomonal system, using a bioinformatics approach. Hydrae were shown to express orthologs of cnidarian phospholipase A2 toxins and cytolysicns belonging to the actinoporin family, and to express proteins similar to elapid-like phospholipases, cysteine-rich secretory proteins (CRISP), prokineticin-like polypeptides and toxic deoxyribonucleases.

The specific sequences responsible for cytotoxic activity in peptides isolated from natural sources have not hitherto been identified.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

As used herein, the terms "comprising" and "including" or grammatical variants thereof are to be taken as specifying the stated features, integers, steps or components but do not preclude the addition of one or more additional features, integers, steps, components or groups thereof. This term encompasses the terms "consisting of" and "consisting essentially of."

The phrase "consisting essentially of" or grammatical variants thereof when used herein are to be taken as specifying the stated features, integers, steps or components but do not preclude the addition of one or more additional features, integers, steps, components or groups thereof but only if the additional features, integers, steps, components or groups thereof do not materially alter the basic and novel characteristics of the claimed composition, device or method.

The term "method" refers to manners, means, techniques and procedures for accomplishing a given task including, but not limited to, those manners, means, techniques and procedures either known to, or readily developed from known manners, means, techniques and procedures by practitioners of the chemical, biological and biophysical arts.

As used herein the term "about" refers to ±10%.

Other features and advantages of the invention will be apparent from the following detailed description, and from the claims.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

Figure 1:
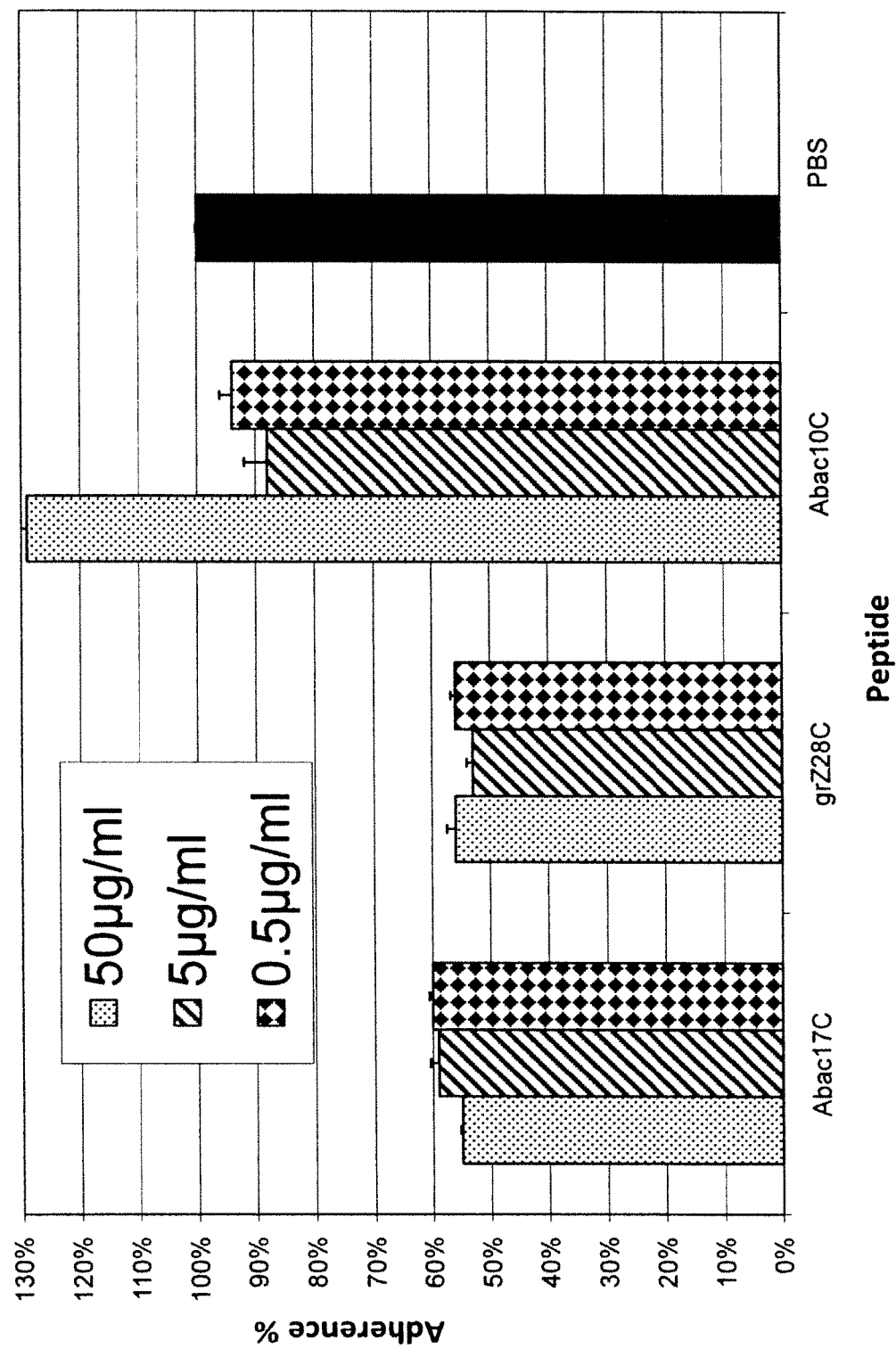
FIG. 1 is a bar graph showing inhibition of adherence of *Pseudomonas aeruginosa* by the synthetic peptide grZ28C [CSFSQNKSVHSFDYDWYNVSDQADLKNC (SEQ ID NO: 1)] at three different concentrations.

The present invention is of compositions comprising a peptide isolated from an animal source, which has one or more effects relating to prevention of bacterial substrate adhesion and the derived biofilm formation, and optionally also prevention of cell-cell adhesion. Other effects may also optionally be provided, additionally or alternatively. The peptide comprises at least the sequence FDYDWY (SEQ ID NO: 2). As a non-limiting example, the peptide may optionally and preferably comprise a sequence selected from the group consisting of FDYDWY (SEQ ID NO: 2), SFSQNKSVHSFDYDWYNVSDQADLKN (SEQ ID NO: 3) or CSFSQNKSVHSFDYDWYNVSDQADLKNC (SEQ ID NO: 1)

One of the major concerns in medicine is microbial biofilm formation. In humans, biofilms are a major concern when introducing products into the body (e.g., contact lenses, central venous catheters, mechanical heart valves and pacemakers).

Biofilms are also a problem in many industries including the food, pharmaceutical, paint, water, shipping and engineering industries causing, amongst a wide range of negative effects, accelerated corrosion in industrial systems, oil souring and biofouling. For example, biofouling may be caused by the adhesion of organisms to any surface in a marine or freshwater environment, including cooling towers, water pipes and filters in cooling or desalinization installations, irrigation and power stations, and membranes, such as those used in wastewater and desalinization systems. Biofouling also occurs in aquaculture systems in fish farms.

Furthermore the commercial shipping fleets of the world consume approximately 300 million tons of fuel annually. Without antifouling measures, that fuel consumption would increase by as much as 40%, equivalent to an extra 120 million tons of fuel annually. The economic cost of this was estimated as about $7.5 billion in 2000; a more recent estimate is $30 billion.

Biofilms are very difficult to eliminate since microbes growing within are highly organized and can withstand hostile environments, such as high temperatures and anti-microbial agents (e.g., antibiotics).

Marine and fresh water plants and organisms including soft bodied water invertebrates, fish and moss are surrounded by broad spectrum species of microbial organisms. Since such plant and organisms lack specific immunity, they produce several factors which can prevent microbial colonization on their body surface.

The most "sensitive" organisms are invertebrates belong to the phylum cnidaria that include the sea anemones, corals, jellyfish, hydroids, medusae, and sea fans. Such soft bodied organism, which lack physical protection such as scales or shells, use proteins and secondary metabolites to protect themselves from the microbial environment surrounding them.

It has been previously reported that marine organisms (e.g. sponges) produce secondary metabolites that exhibit antibacterial and antifungal activities [Amade et al., supra]. Moreover, sea anemones (e.g., *Actinia equina*) have been shown to produce toxic, pore forming peptides (i.e., equinatoxins), which lyse and kill eukaryotic cells similarly to other small antimicrobial peptides [Anderluh et al., supra].

From these natural factors, peptides with high conservation sequences were isolated, and showed high activity in prevention of microbial adherence in its synthetic conformation. The conserved sequence is found in several marine organisms, including various known species of sea anemone, several fish (including *Danio rerio*—zebra fish), and in moss *Physcomitrella patens* subsp. *Patens*.

Based on bioinformatic analysis it is believed that the protein has changed in upper organisms (including *Homo sapiens*) to FDYDWY (SEQ ID NO: 2), that can be found in proteins with size range from 128aa-400aa. In *Homo sapiens* this peptide is part of the G protein-coupled receptor 137B (GENE ID: 7107 GPR137B) located at 269-274. Based on UniProtKB/Swiss-Prot entry O60478 the region, which starts at 259 and ends at 292, is an extracellular region, which supports the theory that this peptide is the active part of the protein.

Bioinformatics analysis of the ancient sea organism Ciona intestinalis identifieda 368 amino acid protein, similar to the G protein-coupled receptor 137ba [GeneBank Accesion number XP_002125109]. The region similar to the anti adhesive peptide is SPLRCSELSSFNFDWYNVSDQADLVN (SEQ ID NO: 4). Based on this information, and the fact that Ciona intestinalis is also exposed to a large diversity of microorganisms, the present inventors hypothesise that the peptide FNFDWY (SEQ ID NO: 5) is also anti adhesive. The non-cyclized peptide sequence SFSQNKSVHSFDYDWYNVSDQADLKN (SEQ ID NO: 3) which represent the extracellular region, residue 259-284, was synthesized with two Cysteines in C and N termini.

The cyclized peptide sequence SFSQNKSVHSFDYDWYNVSDQADLKNQLGDAGYV (SEQ ID NO: 6) which represents the extracellular region, residue 259-292, was synthesized with two Cysteines in C and N termini and S—S bridged.

According to some embodiments, the peptide of the present invention comprises at least the sequence FDYDWY (SEQ ID NO: 2). For example, the peptide may comprise at least one of FDYDWY (SEQ ID NO: 2), SFDYDWY (SEQ ID NO: 7), SFDYDWYN (SEQ ID NO: 8), HSFDYDWYN (SEQ ID NO: 9), HSFDYDWYNV (SEQ ID NO: 10), VHSFDYDWYNV (SEQ ID NO: 11), VHSFDYDWYNVS (SEQ ID NO: 12), SVHSFDYDWYNVS (SEQ ID NO: 13), SVHSFDYDWYNVSD (SEQ ID NO: 14), KSVHSFDYDWYNVSD (SEQ ID NO: 15), KSVHSFDYDWYNVSDQ (SEQ ID NO: 16), NKSVHSFDYDWYNVSDQ (SEQ ID NO: 17), NKSVHSFDYDWYNVSDQA (SEQ ID NO: 18), QNKSVHSFDYDWYNVSDQA (SEQ ID NO: 19), QNKSVHSFDYDWYNVSDQAD (SEQ ID NO: 20), SQNKSVHSFDYDWYNVSDQAD (SEQ ID NO: 21), SQNKSVHSFDYDWYNVSDQADL (SEQ ID NO: 22), FSQNKSVHSFDYDWYNVSDQADL (SEQ ID NO: 23), FSQNKSVHSFDYDWYNVSDQADLK (SEQ ID NO: 24), SFSQNKSVHSFDYDWYNVSDQADLK (SEQ ID NO: 25), SFSQNKSVHSFDYDWYNVSDQADLKN (SEQ ID NO: 3), CSFSQNKSVHSFDYDWYNVSDQADLKN (SEQ ID NO: 26) or CSFSQNKSVHSFDYDWYNVSDQADLKNC (SEQ ID NO: 1), or combinations thereof.

According to some embodiments, the peptide is cyclized.

According to some embodiments, the peptide is non-cyclized.

The peptide may be isolated from any animal. Preferably, the animal is a vertebrate, such as, for example, a fish, an amphibian (including a frog, a toad, a newt or a salamander), a bird, a reptile (such as a crocodilee, a lizard, a snake, a turtle, a tortoise or a *terrapin*) or a mammal (including a human).

The peptide is also present in the sea organism Ciona intestinalis, which belongs to the phylum Chordata. In this organism, the protein shows similarity to the GPCR 137 b in upper vertebrae and since this organism is surrounded by microorganisms,—the peptide that includes the sequence FNFDWY (SEQ ID NO: 5) is also part of the patent.

The peptide of the present invention may optionally comprise at least two of the above sequences, connected by a linker of some type, such that the N-terminal of a first peptide sequence is connected to the C-terminal of the linker, and the C-terminal of a second peptide sequence is connected to the N-terminal of the linker.

As used herein, the term "linker" refers to any chemical bond or molecule for connecting two peptides or for cyclizing a peptide as described herein. The linker may also optionally comprise a polymer of any suitable number of monomeric units. However, in any case preferably the linker features an active group, and/or is derivatized to include such an active group, in at least two locations, so as to join two or more peptides and/or to cyclize a peptide as described herein.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

According to one aspect of the present invention, there is provided a composition comprising a peptide isolated from a human source, the peptide comprising a sequence selected from the group consisting of FDYDWY (SEQ ID NO: 2), SFSQNKSVHSFDYDWYNVSDQADLKN (SEQ ID NO: 3) or CSFSQNKSVHSFDYDWYNVSDQADLKNC (SEQ ID NO: 1).

According to an additional aspect of the present invention there is provided a method of preventing adhesion of a single cell organism to a surface, the method comprising contacting the cell with a composition comprising a peptide isolated from a human source comprising a sequence selected from the group consisting of FDYDWY (SEQ ID NO: 2), SFSQNKSVHSFDYDWYNVSDQADLKN (SEQ ID NO: 3) or CSFSQNKSVHSFDYDWYNVSDQADLKNC (SEQ ID NO: 1), thereby preventing adhesion of a cell to a surface.

According to some embodiments of the present invention, there is preferably provided a domain which comprises at least one of the above peptides and which is effective against cell adhesion to a surface. More preferably, the domain is included as part of a protein. Optionally and most preferably, the domain exhibits anti-adhesive behavior, for example for the prevention of formation and/or treatment of a biofilm, but does not exhibit cytotoxic behavior.

As used herein, the term "isolated" refers to a composition that has been removed from its in-vivo location. Preferably the isolated compositions of the present invention are substantially free from other substances (e.g., other proteins that do not comprise anti-adhesive effects) that are present in their in-vivo location (i.e. purified or semi-purified). The isolated peptides may optionally be synthetic or obtained from natural sources, including optionally by being expressed in-vivo using genetic engineering techniques.

According to some embodiments of the present invention, the compositions of the present invention are devoid of cytotoxic or cytostatic activity, e.g. they are not bactericidal or bacteristatic.

According to some embodiments of the present invention, the compositions of the present invention are resistant to lyophilization—e.g. their activities are preserved following freeze drying.

As used herein the phrase "single cell organism" refers to a unicellular organism also termed a microorganism or a microbe. The single cell organism of the present invention can be a eukaryotic single cell organism (e.g., protozoa or fungi for example yeast) or a prokaryotic single cell organism (e.g., bacteria or archaea). The single cell organisms of the present invention may be in any cellular environment, such as for example, in a biofilm, as isolated cells or as a cell suspension.

As used herein the term "biofilm" refers to an extracellular matrix in which microorganisms are dispersed and/or form colonies. The biofilm typically is made of polysaccharides and other macromolecules.

Exemplary bacterial cells, whose adhesion may be prevented according to the method of the present invention, include gram positive bacteria and gram negative bacteria.

The term "Gram-positive bacteria" as used herein refers to bacteria characterized by having as part of their cell wall structure peptidoglycan as well as polysaccharides and/or teichoic acids and are characterized by their blue-violet color reaction in the Gram-staining procedure. Representative Gram-positive bacteria include: *Actinomyces* spp., *Bacillus anthracia, Bifidobacterium* spp., *Clostridium botulinum, Clostridium perfringens, Clostridium* spp., *Clostridium tetani, Corynebacterium diphtheriae, Corynebacterium jeikeium, Enterococcus faecalis, Enterococcus faecium, Erysipelothrix rhusiopathiae, Eubacterium* spp., *Gardnerella vaginalis, Gemella morbillorum, Leuconostoc* spp., *Mycobacterium abscessus, Mycobacterium avium complex, Mycobacterium chelonae, Mycobacterium fortuitum, Mycobacterium haemophilium, Mycobacterium kansasii, Mycobacterium leprae, Mycobacterium marinum, Mycobacterium scrofulaceum, Mycobacterium smegmatis, Mycobacterium terrae, Mycobacterium tuberculosis, Mycobacterium ulcerans, Nocardia* spp., *Peptococcus niger, Peptostreptococcus* spp., *Proprionibacterium* spp., *Sarcina lutea, Staphylococcus aureus, Staphylococcus auricularis, Staphylococcus capitis, Staphylococcus cohnii, Staphylococcus epidermidis, Staphylococcus haemolyticus, Staphylococcus hominis, Staphylococcus lugdanensis, Staphylococcus saccharolyticus, Staphylococcus saprophyticus, Staphylococcus schleiferi, Staphylococcus similans, Staphylococcus warneri, Staphylococcus xylosus, Streptococcus agalactiae* (group B *streptococcus*), *Streptococcus anginosus, Streptococcus bovis, Streptococcus canis, Streptococcus equi, Streptococcus milleri, Streptococcus mitior, Streptococcus mutans, Streptococcus pneumoniae, Streptococcus pyogenes* (group A *streptococcus*), *Streptococcus salivarius, Streptococcus sanguis*.

The term "Gram-negative bacteria" as used herein refer to bacteria characterized by the presence of a double membrane surrounding each bacterial cell. Representative Gram-negative bacteria include *Acinetobacter calcoaceticus, Acinetobacter baumannii, Actinobacillus actinomycetemcomitans, Aeromonas hydrophila, Alcaligenes xylosoxidans, Bacteroides, Bacteroides fragilis, Bartonella bacilliformis, Bordetella* spp., *Borrelia burgdorferi, Branhamella catarrhalis, Brucella* spp., *Campylobacter* spp., *Chalmydia pneumoniae, Chlamydia psittaci, Chlamydia trachomatis, Chromobacterium violaceum, Citrobacter* spp., *Eikenella corrodens, Enterobacter aerogenes, Escherichia coli, Flavobacterium meningosepticum, Fusobacterium* spp., *Haemophilus influenzae, Haemophilus* spp., *Helicobacter pylori, Klebsiella pneumoniae, Klebsiella* spp., *Legionella* spp., *Leptospira* spp., *Moraxella catarrhalis, Morganella morganii, Mycoplasma pneumoniae, Neisseria gonorrhoeae, Neisseria meningitidis, Pasteurella multocida, Plesiomonas shigelloides, Prevotella* spp., *Proteus* spp., *Providencia rettgeri, Pseudomonas aeruginosa, Pseudomonas* spp., *Rickettsia prowazekii, Rickettsia rickettsii, Rochalimaea* spp., *Salmonella* spp., *Salmonella typhi, Serratia marcescens, Shigella* spp., *Shigella sonnei, Treponema carateum, Treponema pallidum, Treponema pallidum endemicum, Treponema pertenue, Veillonella* spp., *Vibrio cholerae, Vibrio vulnificus, Yersinia enterocolitica, Yersinia pestis*.

The term "fungi" as used herein refers to the heterotrophic organisms characterized by the presence of a chitinous cell wall, and in the majority of species, filamentous growth as multicellular hyphae. Representative fungi whose adhesion may be prevented according to the method of the present invention include *Candida albicans, Saccharomyces cerevisiae, Candida glabrata, Candida parapsilosis* and *Candida dubliniensis*.

As used herein the phrase "preventing adhesion" refers to reducing or eliminating cell attachment to a surface (e.g. by reducing the rate of growth on a surface). Preferably, the compositions of the present invention prevent cell adhesion by as much as 10%, more preferably by 20%, more preferably by 30%, more preferably by 40%, more preferably by 50%, more preferably by 60%, more preferably by 70%, more preferably by 80%, more preferably by 90% and most preferably by 100% as measured by a cell adhesion assay. Exemplary cell adhesion assays are described herein below and in the Examples section that follows. It will be appreciated that the compositions of the present invention may also be capable of preventing cell aggregation (i.e. cell aggregation not to a surface).

The present invention contemplates prevention of cellular adhesion to a wide variety of surfaces including fabrics, fibers, foams, films, concretes, masonries, glass, metals, plastics, polymers, and like.

According to one embodiment, the surface is comprised in a device that is susceptible to biofilm formation. Exemplary devices whose surfaces are contemplated by the present invention include, but are not limited to, vessel hulls, automobile surfaces, air plane surfaces, membranes, filters, and industrial equipment.

The surface may also be comprised in medical devices, instruments, and implants. Examples of such medical devices, instruments, and implants include any object that is capable of being implanted temporarily or permanently into a mammalian organism, such as a human. Representative medical devices, instruments, and implants that may be used according to the present invention include, for example, central venous catheters, urinary catheters, endotracheal tubes, mechanical heart valves, pacemakers, vascular grafts, stents and prosthetic joints. Methods of preventing cell attachment to medical devices and further examples thereof are described herein below.

As mentioned, the method of the present invention is effected by contacting the cell with a composition from an organism capable of preventing adhesion of the cell to a surface.

As used herein the term "contacting" refers to the positioning of the compositions of the present invention such that they are in direct or indirect contact with the adhesive cells in such a way that the active agent comprised within is able to prevent adhesion of cells thereto. Thus, the present invention contemplates both applying the compositions of the present invention to a desirable surface and/or directly to the adhesive cells.

Contacting the compositions with a surface can be effected using any method known in the art including spraying, spreading, wetting, immersing, dipping, painting, ultrasonic welding, welding, bonding or adhering. The compositions of the present invention may be attached as monolayers or multiple layers.

According to other embodiments of the present invention, the above peptides may optionally be altered so as to form non-peptide analogs, including but not limited to replacing one or more bonds with less labile bonds, cyclization (described in greater detail below) and the like. Additionally or alternatively, a peptide may optionally be converted to a small molecule through computer modeling, as described for example in PCT Application No. WO/2007/147098, hereby incorporated by reference as if fully set forth herein.

A "peptidomimetic organic moiety" can optionally be substituted for amino acid residues in a peptide according to the present invention both as conservative and as non-conservative substitutions. These moieties are also termed "non-natural amino acids" and may optionally replace amino acid residues, amino acids or act as spacer groups within the peptides in lieu of deleted amino acids. The peptidomimetic organic moieties optionally and preferably have steric, electronic or configurational properties similar to the replaced amino acid and such peptidomimetics are used to replace amino acids in the essential positions, and are considered conservative substitutions. However such similarities are not necessarily required. The only restriction on the use of peptidomimetics is that the composition at least substantially retains its physiological activity as compared to the native peptide according to the present invention.

Peptidomimetics may optionally be used to inhibit degradation of the peptides by enzymatic or other degradative processes. The peptidomimetics can optionally and preferably be produced by organic synthetic techniques. Non-limiting examples of suitable peptidomimetics include D amino acids of the corresponding L amino acids, tetrazol (Zabrocki et al., J. Am. Chem. Soc. 110:5875 5880 (1988)); isosteres of amide bonds (Jones et al., Tetrahedron Lett. 29: 3853 3856 (1988)); LL 3 amino 2 propenidone 6 carboxylic acid (LL Acp) (Kemp et al., J. Org. Chem. 50:5834 5838 (1985)). Similar analogs are shown in Kemp et al., Tetrahedron Lett. 29:5081 5082 (1988) as well as Kemp et al., Tetrahedron Lett. 29:5057 5060 (1988), Kemp et al., Tetrahedron Lett. 29:4935 4938 (1988) and Kemp et al., J. Org. Chem. 54:109 115 (1987). Other suitable but exemplary peptidomimetics are shown in Nagai and Sato, Tetrahedron Lett. 26:647 650 (1985); Di Maio et al., J. Chem. Soc. Perkin Trans., 1687 (1985); Kahn et al., Tetrahedron Lett. 30:2317 (1989); Olson et al., J. Am. Chem. Soc. 112:323 333 (1990); Garvey et al., J. Org. Chem. 56:436 (1990). Further suitable exemplary peptidomimetics include hydroxy 1,2,3,4 tetrahydroisoquinoline 3 carboxylate (Miyake et al., J. Takeda Res. Labs 43:53 76 (1989)); 1,2,3,4 tetrahydro-isoquinoline 3 carboxylate (Kazmierski et al., J. Am. Chem. Soc. 133: 2275 2283 (1991)); histidine isoquinolone carboxylic acid (HIC) (Zechel et al., Int. J. Pep. Protein Res. 43 (1991)); (2S, 3S) methyl phenylalanine, (2S, 3R) methyl phenylalanine, (2R, 3S) methyl phenylalanine and (2R, 3R) methyl phenylalanine (Kazmierski and Hruby, Tetrahedron Lett. (1991).

Exemplary, illustrative but non-limiting non-natural amino acids include beta-amino acids (beta3 and beta2), homo-amino acids, cyclic amino acids, aromatic amino acids, Pro and Pyr derivatives, 3-substituted Alanine derivatives, Glycine derivatives, ring-substituted Phe and Tyr Derivatives, linear core amino acids or diamino acids. They are available from a variety of suppliers, such as Sigma-Aldrich (USA) for example.

In the present invention any part of a peptide may optionally be chemically modified, i.e. changed by addition of functional groups. The modification may optionally be performed during synthesis of the molecule if a chemical synthetic process is followed, for example by adding a chemically modified amino acid. However, chemical modification of an amino acid when it is already present in the molecule ("in situ" modification) is also possible.

The amino acid of any of the sequence regions of the molecule can optionally be modified according to any one of the following exemplary types of modification (in the peptide conceptually viewed as "chemically modified"). Non-limiting exemplary types of modification include carboxymethylation, acylation, phosphorylation, glycosylation or fatty acylation. Ether bonds can optionally be used to join the serine or threonine hydroxyl to the hydroxyl of a sugar. Amide bonds can optionally be used to join the glutamate or aspartate carboxyl groups to an amino group on a sugar (Garg and Jeanloz, Advances in Carbohydrate Chemistry and Biochemistry, Vol. 43, Academic Press (1985); Kunz, Ang. Chem. Int. Ed. English 26:294-308 (1987)). Acetal and ketal bonds can also optionally be formed between amino acids and carbohydrates. Fatty acid acyl derivatives can optionally be made, for example, by acylation of a free amino group (e.g., lysine) (Toth et al., Peptides: Chemistry, Structure and Biology, Rivier and Marshal, eds., ESCOM Publ., Leiden, 1078-1079 (1990)).

As used herein the term "chemical modification," when referring to a peptide according to the present invention, refers to a peptide where at least one of its amino acid residues is modified either by natural processes, such as processing or other post-translational modifications, or by chemical modification techniques which are well known in the art. Examples of the numerous known modifications typically include, but are not limited to: acetylation, acylation, amidation, ADP-ribosylation, glycosylation, GPI anchor formation, covalent attachment of a lipid or lipid derivative, methylation, myristylation, pegylation, prenylation, phosphorylation, ubiquitination, or any similar process.

As mentioned, medical devices and implants are commonly infected with opportunistic bacteria and other infectious microorganisms (e.g., fungi) in some cases necessitating the removal of implantable devices. Such infections can also result in illness, long hospital stays, or even death. The prevention of biofilm formation and infection of medical devices is therefore highly desirous.

Thus, the present invention also contemplates medical devices in which the above-described compositions are attached thereto.

As used herein the term "medical device" refers to any implant, instrument, apparatus, implement, machine, device or any other similar or related object (including any component or accessory), which is intended for use in the diagnosis, treatment, cure or prevention of disease or other conditions. Such medical device is intended for use in man or other animals and is anticipated to affect the structure or any function of the body. Such medical device does not achieve its primary intended purposes through chemical action and is not dependent upon being metabolized for the achievement of its primary intended purposes.

As used herein the term "implant" refers to any object intended for placement in a human body that is not a living tissue. The implant may be temporary or permanent. An implant can be an article comprising artificial components, such as catheters or pacemakers. Implants can also include naturally derived objects that have been processed so that their living tissues have been devitalized. As an example, bone grafts that have been processed so that their living cells are removed (acellularized), but so that their shape is retained to serve as a template for ingrowth of bone from a host. As another example, naturally occurring coral can be processed to yield hydroxyapatite preparations that can be applied to the body for certain orthopedic and dental therapies.

The present invention therefore envisions coating medical devices with the compositions of the present invention to prevent cell adherence thereto so as to reduce/eliminate any possible cell aggregation and biofilm formation known to occur following implantation. Device-related infections usually result from the introduction of microorganisms, primarily bacteria, during the device insertion or implantation procedure, or from attachment of blood-borne organisms to the newly inserted device and their subsequent propagation on its surface. Coating the medical device with the compositions of the present invention will therefore inhibit biofilm formation of one or more microbial species, will prevent medical device related infections, and consequently will reduce the need of antibiotic treatment or removal of the medical device from the subject.

Medical devices that may be coated according to the teachings of the present invention include, but not limiting to, artificial blood vessels, catheters and other devices for the removal or delivery of fluids to patients, artificial hearts, artificial kidneys, orthopedic pins, prosthetic joints, plates and implants; catheters and other tubes (including urological and biliary tubes, endotracheal tubes, peripherably insertable central venous catheters, dialysis catheters, long term tunneled central venous catheters, peripheral venous catheters, short term central venous catheters, arterial catheters, pulmonary catheters, Swan-Ganz catheters, urinary catheters, peritoneal catheters), urinary devices (including long term urinary devices, tissue bonding urinary devices, artificial urinary sphincters, urinary dilators), shunts (including ventricular or arterio-venous shunts); prostheses (including breast implants, penile prostheses, vascular grafting prostheses, aneurysm repair devices, mechanical heart valves, artificial joints, artificial larynxes, otological implants), anastomotic devices, vascular catheter ports, vascular stents, clamps, embolic devices, wound drain tubes, ocular lenses, dental implants, hydrocephalus shunts, pacemakers and implantable defibrillators, needleless connectors, voice prostheses and the like.

Another possible application of the compositions of the present invention is the coating of surfaces found in the medical and dental environment. Such surfaces include the inner and outer aspects of various instruments and devices, whether disposable or intended for repeated uses. Such surfaces include the entire spectrum of articles adapted for medical use, including without limitation, scalpels, needles, scissors and other devices used in invasive surgical, therapeutic or diagnostic procedures; blood filters. Other examples will be readily apparent to practitioners in these arts.

Surfaces found in the medical environment also include the inner and outer aspects of pieces of medical equipment, medical gear worn or carried by personnel in the health care setting. Such surfaces can include surfaces intended as biological barriers to infectious organisms in medical settings, such as gloves, aprons and faceshields. Commonly used materials for biological barriers are thermoplastic or polymeric materials such as polyethylene, dacron, nylon, polyesters, polytetrafluoroethylene, polyurethane, latex, silicone and vinyl. Other surfaces can include counter tops and fixtures in areas used for medical procedures or for preparing medical apparatus, tubes and canisters used in respiratory treatments, including the administration of oxygen, of solubilized drugs in nebulizers and of anesthetic agents. Other such surfaces can include handles and cables for medical or dental equipment not intended to be sterile. Additionally, such surfaces can include those non-sterile external surfaces of tubes and other apparatus found in areas where blood or body fluids or other hazardous biomaterials are commonly encountered.

The compositions of the present invention can be used on the surface of or within these medical devices to provide long term protection against microorganism colonization and reduce the incidence of device-related infections. These compositions can also be incorporated in combination with an anti-microbial agent (e.g., antibiotic agent) into coatings for medical devices. Such a combination will sufficiently kill or inhibit the initial colonizing bacteria and prevent device-related infections as long as the substance is presented in an inhibitory concentration at the device-microbe interface.

The compositions of the present invention can be directly incorporated into the polymeric matrix of the medical device at the polymer synthesis stage or at the device manufacture stage. The compositions can also be covalently attached to the medical device polymer. These and many other methods of coating medical devices are evident to one of ordinary skill in the art.

Additional surfaces that can be treated according to the teachings of the present invention include the inner and outer aspects of those articles involved in water purification, water storage and water delivery, and those articles involved in food processing. Thus the present invention envisions coating a solid surface of a food or beverage container to extend the shelf life of its contents.

Surfaces related to health can also include the inner and outer aspects of those household articles involved in providing for nutrition, sanitation or disease prevention. Thus, the compositions of the present invention can be used for removal of disease-causing microorganisms from external surfaces. These can include, for example food processing equipment for home use, materials for infant care, tampons, soap, detergents, health and skincare products, household cleaners and toilet bowls.

The surface may be also be laboratory articles including, but not limited to, microscopic slide, a culturing hood, a Petri dish or any other suitable type of tissue culture vessel or container known in the art.

The inventors of this application also envision the use of the compositions of the present invention as anti-fouling agents.

As used herein the term "anti-fouling agents" refers to the compounds used to protect underwater surfaces from attaching single cell organisms. These single cell organisms include microorganism such as bacteria and fungi.

These underwater surfaces include any water immersed surface, including ships'/boats's hulls (i.e., the body or frame of a ship or boat), submergence vehicles, navigational aids, screens, nets, constructions, floating or emplaced off-shore platforms (e.g., docks), buoys, signaling equipment and articles which come into contact with sea water or salty water. Other underwater surfaces include structures exposed to sea water including pilings, marine markers, undersea conveyances like cabling and pipes, fishing nets, bulkheads, cooling towers, and any device or structure that operates submerged.

The compositions of the present invention can be incorporated into marine coatings to limit undesirable marine fouling. Thus, the anti-fouling agents of the present invention can be formulated so as not to contain toxic materials (such as heavy metals), and still retain their efficacy. The anti-fouling paint of the present invention may further contain binders(s), pigment(s), solvent(s) and additive(s).

Examples of solvents that may be used include aromatic hydrocarbons such as xylene and toluene; aliphatic hydrocarbons such as hexane and heptane, esters such as ethyl acetate and butyl acetate; amides such as N-methylpyrrolidone and N,N-dimethylformamide; alcohols such as isopropyl alcohol and butyl alcohol; ethers such as dioxane, THF and diethyl ether; and ketones such as methyl ethyl ketone, methyl isobutyl ketone and methyl isoamyl ketone. The solvents may be used alone or in combination thereof.

Examples of binders that may be used include alkyd resin, acrylic or vinyl emulsions, polyurethane resins, epoxy resins, silicone based resins, acrylic resins, inorganic silicate based resins, vinyl resins, particularly a vinyl chloride/vinyl acetate copolymer, and rosin.

Examples of pigments that may be used include titanium dioxide, cuprous oxide, iron oxide, talc, aluminium flakes, mica flakes, ferric oxide, cuprous thiocyanate, zinc oxide, cupric acetate meta-arsenate, zinc chromate, zinc dimethyl dithiocarbamate, zinc ethylene bis(dithiocarbamate) and zinc diethyl dithiocarbamate.

Examples of additives that may be incorporated into the coating composition include dehumidifiers, wetting/dispersing agents, anti-settling agents, anti-skinning agents, drying/curing agents, anti-marring agents and additives ordinarily employed in coating compositions as stabilizers and anti-foaming agents. Additionally, any antibiotic which is relatively insoluble in seawater can be used with an anti-fouling marine paint.

Methods of preparing marine anti-fouling paints are explained in detail in U.S. Pat. Nos. 4,678,512; 4,286,988; 4,675,051; 4,865,909; and 5,143,545.

The compositions of the present invention may also be used for providing antibacterial properties in cosmetics, to prevent spoiling of the product.

The compositions may further be used to provide an antibacterial effect to the mouth, teeth and gums, such as by incorporation in a toothpaste, mouthwash, or chewing gum. Taken together the present teachings portray a wide range of novel anti-adhesive agents isolated from organisms such as aquatic organisms and moss. The broad spectrum of the anti adhesion effects of these agents (e.g. inhibiting adhesion of gram positive and gram negative bacteria) together with their ability to effect the initial, vulnerable stages of microbial biofilm formation, makes these agents prime candidates as anti-biofilm agents. Moreover, the anti-adhesive agents described herein are clonable enabling modifications and mass production thereof. In addition their stability (i.e. resistance to environmental conditions) makes these agents suitable for a diverse array of applications.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology," John Wiley and Sons, Baltimore, Md. (1989); Perbal, "A Practical Guide to Molecular Cloning," John Wiley & Sons, New York (1988); Watson et al., "Recombinant DNA," Scientific American Books, New York; Birren et al. (eds) "Genome Analysis: A Laboratory Manual Series," Vols. 1-4, Cold Spring Harbor Laboratory Press, New York (1998); methodologies as set forth in U.S. Pat. Nos. 4,666,828; 4,683,202; 4,801,531; 5,192,659 and 5,272, 057; "Cell Biology: A Laboratory Handbook," Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology," W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications," Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

EXAMPLES

Reference is now made to the following examples, which together with the above description, illustrate the invention in a non limiting fashion.

Example 1: Prevention of Bacterial Attachment by grZ28C

The synthetic peptide grZ28C [C SFSQNKSVHSFDYD-WYNVSDQADLKNC (SEQ ID NO: 1)] gave approximately 50% prevention of *Pseudomonas aeruginosa* attachment at three concentrations: 50, 5 and 0.5 µg/ml (FIG. 1). The activity was similar to that of the AbacZ17C, peptide based on the anemone cytotoxin active region. Abac10C, which was used as a negative control peptide, was synthesized based on the N-terminal sequence of Abac17C, without the active residue [CMFSVPFDYC (SEQ ID NO: 27)].

Figure 2:
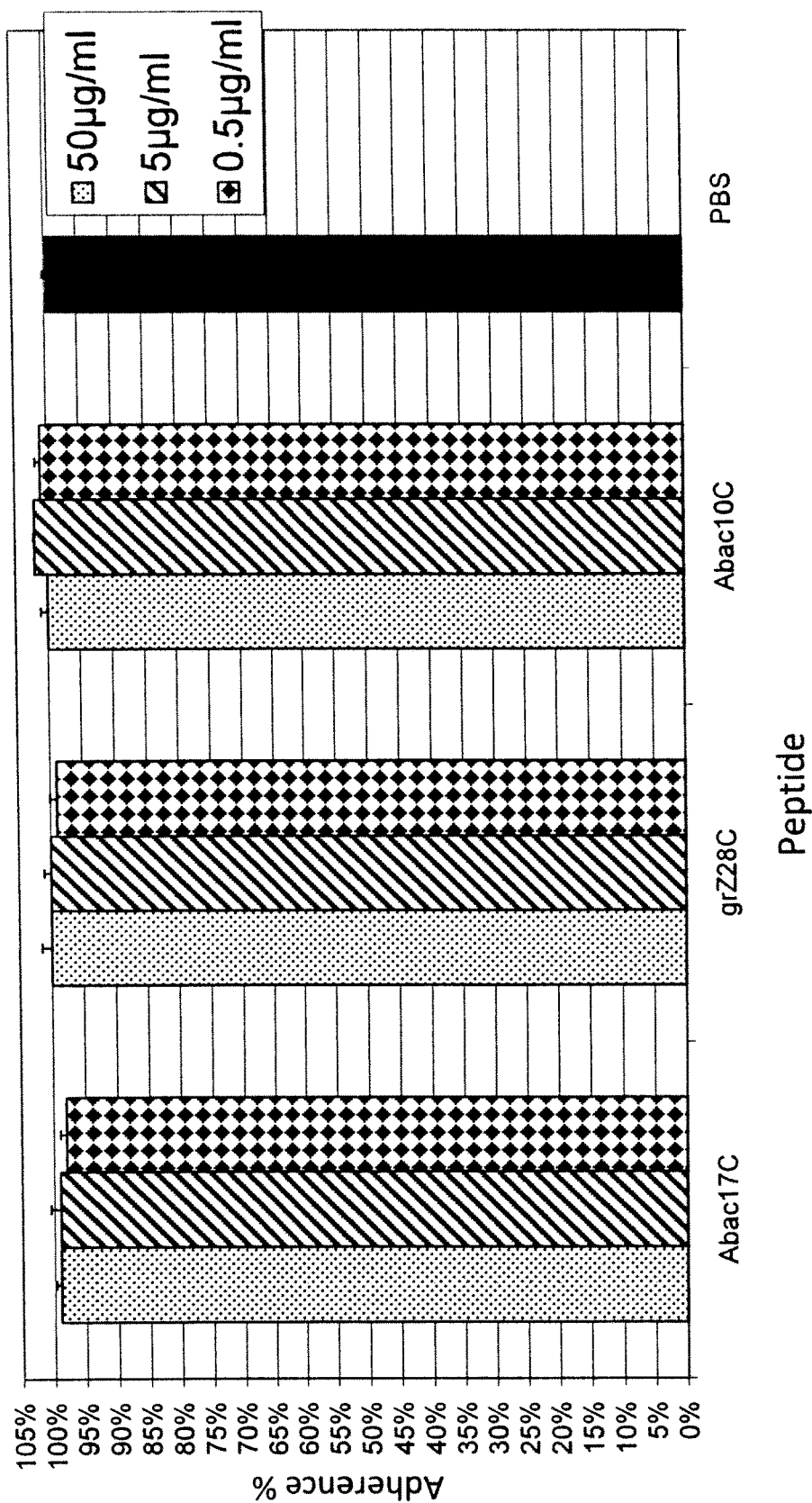
FIG. 2 is bar graph shows a growth test on *Pseudomonas aeruginosa*.

FIG. 2 demonstrates that no growth effect occurs in the presence of the test peptides.

Figure 3:
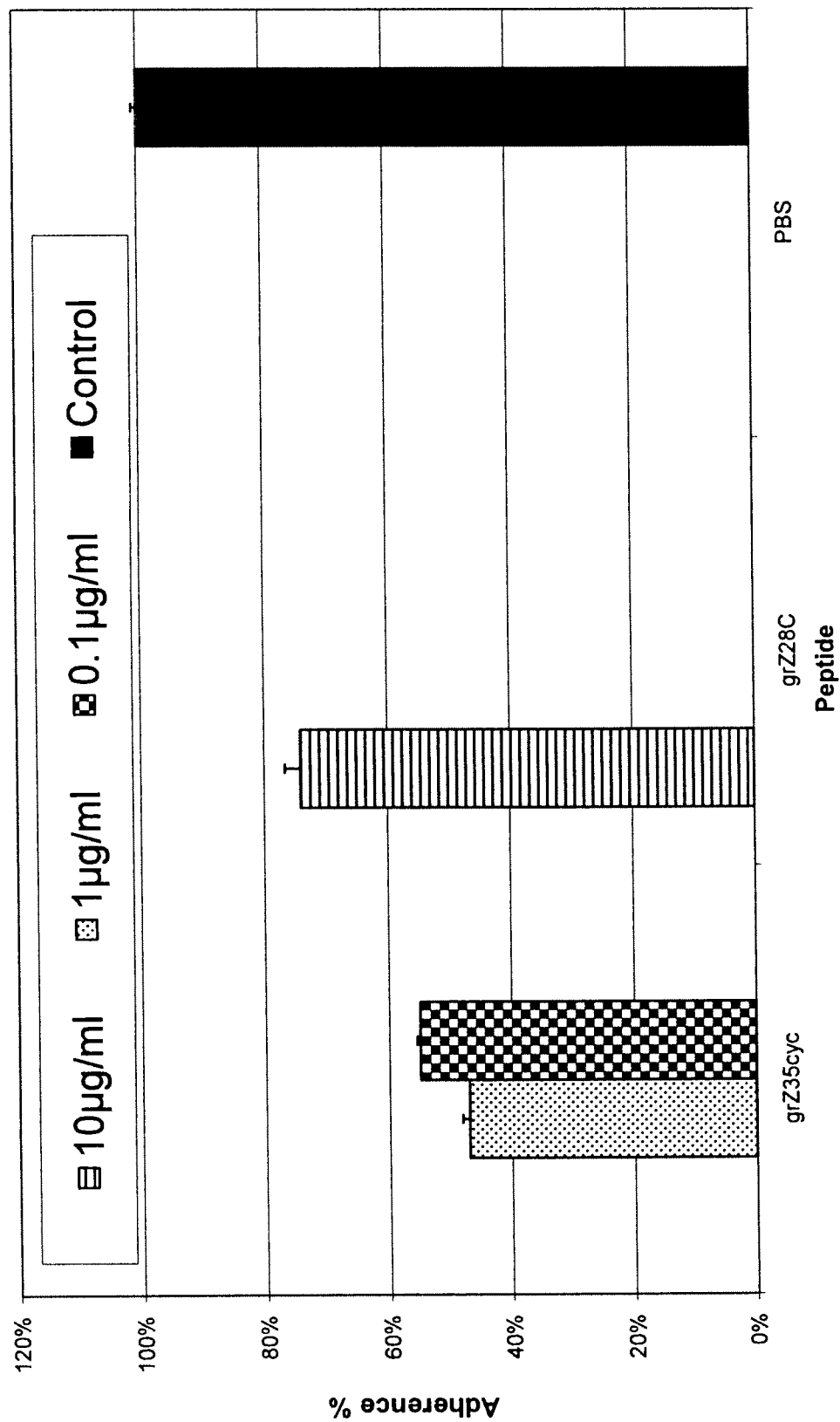
FIG. 3 is a bar graph showing anti-adherence activity of peptides grZ35 cyc and grZ28C based on the amino acid sequence of GPCR 137b on *Pseudomonas aeruginosa*.

FIG. 3 shows anti adherence activity with peptides grZ35 cyc and grZ28C, based on the amino acid sequence of GPCR 137b on *P. aeruginosa*. For peptide grZ35 cyc, the peptide sequence SFSQNKSVHSFDYDWYNVSDQADLKNQL-GDAGYV (SEQ ID NO: 6) which represents the extracellular region, residue 259-292, was synthesized with two Cysteines in the C and N termini and S—S bridged. For peptide grZ28C, the peptide sequence SFSQNKSVHSFDY-DWYNVSDQADLKN (SEQ ID NO: 3) which represents the extracellular region, residue 259-284, was synthesized with two Cysteines in C and N termini.

Figure 4:
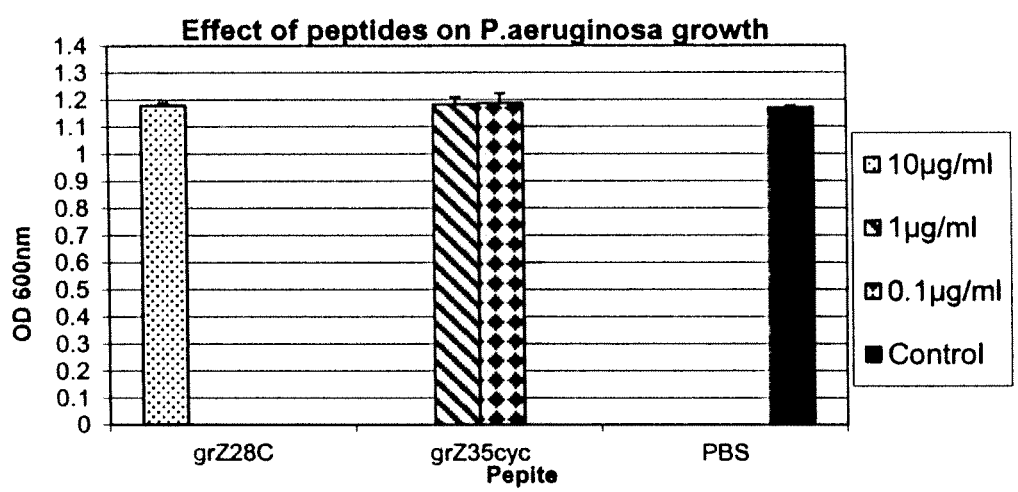
FIG. 4 is a bar graph showing the effects of peptides grZ35 cyc and grZ28C on *P. aeruginosa* growth.

FIG. 4 shows the effects of peptides grZ35 cyc and grZ28C on *P. aeruginosa* growth, indicating that growth of the bacteria was not inhibited. This result is important as peptides of the present invention desirably show little or no growth inhibition of bacteria.

While the invention has been described with respect to a limited number of embodiments, it will be appreciated that many variations, modifications and other applications of the invention may be made.

I claim:

1. A surface coated with a composition comprising a peptide comprising an amino acid sequence selected from the group consisting of FDYDWY (SEQ ID NO: 2), FNFDWY (SEQ ID NO: 5), and combinations thereof, wherein the surface is a medical device, and wherein the medical device is selected from the group consisting of artificial blood vessels, catheters and other devices for the removal or delivery of fluids to patients, artificial hearts, artificial kidneys, orthopedic pins, prosthetic joints, plates, urinary devices, ventricular or arterio-venous shunts, prostheses, breast implants, penile prostheses, vascular grafting prostheses, aneurysm repair devices, mechanical heart valves, artificial joints, artificial larynxes, otological implants, anastomotic devices, vascular catheter ports, vascular stents, clamps, embolic devices, wound drain tubes, ocular lenses, dental implants, hydrocephalus shunts, pacemakers and implantable defibrillators, needleless connectors, and voice prostheses.

2. The surface of claim 1, wherein the catheter is selected from the group consisting of urological tubes, biliary tubes, endotracheal tubes, peripherably insertable central venous catheters, dialysis catheters, long term tunneled central venous catheters, peripheral venous catheters, short term central venous catheters, arterial catheters, pulmonary catheters, Swan-Ganz catheters, urinary catheters, and peritoneal catheters.

3. The surface of claim 1, wherein the medical device is an ocular lens.

4. The surface of claim 1, wherein the peptide is cyclized.

5. The surface of claim 4, wherein the peptide is cyclized via a linker attached to the C and N termini.

6. The surface of claim 1, wherein the peptide is up to 35 amino acids in length.

7. The surface of claim 6, wherein the peptide comprises FDYDWY (SEQ ID NO: 2).

8. The surface of claim 6, wherein the peptide comprises FNFDWY (SEQ ID NO: 5) and is up to 26 amino acids in length.

9. A medical device comprising a polymeric matrix into which a composition comprising a peptide comprising an amino acid sequence selected from the group consisting of FDYDWY (SEQ ID NO: 2), FNFDWY (SEQ ID NO: 5), and combinations thereof is incorporated.

10. The medical device of claim 9, wherein the medical device is selected from the group consisting of artificial blood vessels, catheters and other devices for the removal or delivery of fluids to patients, artificial hearts, artificial kidneys, orthopedic pins, prosthetic joints, plates, urinary devices, ventricular or arterio-venous shunts, prostheses, breast implants, penile prostheses, vascular grafting prostheses, aneurysm repair devices, mechanical heart valves, artificial joints, artificial larynxes, otological implants, anastomotic devices, vascular catheter ports, vascular stents, clamps, embolic devices, wound drain tubes, ocular lenses, dental implants, hydrocephalus shunts, pacemakers and implantable defibrillators, needleless connectors, and voice prostheses.

11. The medical device of claim 10, wherein the catheter is selected from the group consisting of urological tubes, biliary tubes, endotracheal tubes, peripherally-insertable central venous catheters, dialysis catheters, long term tunneled central venous catheters, peripheral venous catheters, short term central venous catheters, arterial catheters, pulmonary catheters, Swan-Ganz catheters, urinary catheters, and peritoneal catheters.

12. The medical device of claim 9, wherein the medical device is an ocular lens.

13. The medical device of claim 9, wherein the peptide is cyclized.

14. The medical device of claim 13, wherein the peptide is cyclized via a linker attached to the C and N termini.

15. The medical device of claim 9, wherein the peptide is up to 35 amino acids in length.

16. The medical device of claim 15, wherein the peptide comprises FDYDWY (SEQ ID NO: 2).

17. The medical device of claim 15, wherein the peptide comprises FNFDWY (SEQ ID NO: 5) and is up to 26 amino acids in length.

18. A surface coated with a composition comprising a peptide comprising an amino acid sequence selected from the group consisting of FDYDWY (SEQ ID NO: 2), FNFDWY (SEQ ID NO: 5), and combinations thereof, wherein the peptide is up to 35 amino acids in length.

19. The surface of claim 18, wherein the surface is a medical device; a laboratory article; a household article; an article involved in water purification, water storage, or water delivery; or an article involved in food processing.

20. The surface of claim 19, wherein the medical device is selected from the group consisting of artificial blood vessels, catheters and other devices for the removal or delivery of fluids to patients, artificial hearts, artificial kidneys, orthopedic pins, prosthetic joints, plates, urinary devices, ventricular or arterio-venous shunts, prostheses, breast implants, penile prostheses, vascular grafting prostheses, aneurysm repair devices, mechanical heart valves, artificial joints, artificial larynxes, otological implants, anastomotic devices, vascular catheter ports, vascular stents, clamps, embolic devices, wound drain tubes, ocular lenses, dental implants, hydrocephalus shunts, pacemakers and implantable defibrillators, needleless connectors, and voice prostheses.

21. The surface of claim 20, wherein the catheter is selected from the group consisting of urological tubes, biliary tubes, endotracheal tubes, peripherably insertable central venous catheters, dialysis catheters, long term tunneled central venous catheters, peripheral venous catheters, short term central venous catheters, arterial catheters, pulmonary catheters, Swan-Ganz catheters, urinary catheters, and peritoneal catheters.

22. The surface of claim 19, wherein the medical device is an ocular lens.

23. The surface of claim 19, wherein the household article is selected from the group consisting of food processing equipment for home use, materials for infant care, tampons, soap, detergents, health and skincare products, household cleaners and toilet bowls.

24. The surface of claim 19, wherein the laboratory article is selected from the group consisting of microscopic slide, a culturing hood, and a tissue culture vessel or container.

25. The surface of claim 24, wherein the tissue culture vessel or container is a Petri dish.

26. The surface of claim 18, wherein the surface is immersed in water.

27. The surface of claim 26, wherein the surface is selected from the group consisting of ships'/boats's hulls, submergence vehicles, navigational aids, screens, nets, constructions, floating or emplaced offshore platforms, buoys, signaling equipment and articles which come into contact with sea water or salty water, pilings, marine markers, cabling, pipes, fishing nets, bulkheads, and cooling towers.

28. The surface of claim 18, wherein the peptide is cyclized.

29. The surface of claim 28, wherein the peptide is cyclized via a linker attached to the C and N termini.

30. The surface of claim 18, wherein the peptide comprises FDYDWY (SEQ ID NO: 2).

31. The surface of claim 18, wherein the peptide comprises FNFDWY (SEQ ID NO: 5) and is up to 26 amino acids in length.

* * * * *

SEQUENCE LISTING

<160> NUMBER OF SEQ ID NOS: 27

<210> SEQ ID NO 1
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Cys Ser Phe Ser Gln Asn Lys Ser Val His Ser Phe Asp Tyr Asp Trp
1               5                   10                  15

Tyr Asn Val Ser Asp Gln Ala Asp Leu Lys Asn Cys
            20                  25

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Phe Asp Tyr Asp Trp Tyr
1               5

<210> SEQ ID NO 3
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ser Phe Ser Gln Asn Lys Ser Val His Ser Phe Asp Tyr Asp Trp Tyr
1               5                   10                  15

Asn Val Ser Asp Gln Ala Asp Leu Lys Asn
            20                  25

<210> SEQ ID NO 4
<211> LENGTH: 26
<212> TYPE: PRT
<213> ORGANISM: Ciona intestinalis

<400> SEQUENCE: 4

Ser Pro Leu Arg Cys Ser Glu Leu Ser Ser Phe Asn Phe Asp Trp Tyr
1               5                   10                  15

Asn Val Ser Asp Gln Ala Asp Leu Val Asn
            20                  25

<210> SEQ ID NO 5
<211> LENGTH: 6
<212> TYPE: PRT
<213> ORGANISM: Ciona intestinalis

<400> SEQUENCE: 5

Phe Asn Phe Asp Trp Tyr
1               5

<210> SEQ ID NO 6
<211> LENGTH: 34
<212> TYPE: PRT

```
<213> ORGANISM: Artificial Sequence
<220> FEATURE:
<223> OTHER INFORMATION: Description of Artificial Sequence: Synthetic
      polypeptide

<400> SEQUENCE: 6

Ser Phe Ser Gln Asn Lys Ser Val His Ser Phe Asp Tyr Asp Trp Tyr
1               5                   10                  15

Asn Val Ser Asp Gln Ala Asp Leu Lys Asn Gln Leu Gly Asp Ala Gly
            20                  25                  30

Tyr Val

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ser Phe Asp Tyr Asp Trp Tyr
1               5

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ser Phe Asp Tyr Asp Trp Tyr Asn
1               5

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

His Ser Phe Asp Tyr Asp Trp Tyr Asn
1               5

<210> SEQ ID NO 10
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

His Ser Phe Asp Tyr Asp Trp Tyr Asn Val
1               5                   10

<210> SEQ ID NO 11
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 11

Val His Ser Phe Asp Tyr Asp Trp Tyr Asn Val
1               5                   10

<210> SEQ ID NO 12
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Val His Ser Phe Asp Tyr Asp Trp Tyr Asn Val Ser
1               5                   10

<210> SEQ ID NO 13
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ser Val His Ser Phe Asp Tyr Asp Trp Tyr Asn Val Ser
1               5                   10

<210> SEQ ID NO 14
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ser Val His Ser Phe Asp Tyr Asp Trp Tyr Asn Val Ser Asp
1               5                   10

<210> SEQ ID NO 15
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Lys Ser Val His Ser Phe Asp Tyr Asp Trp Tyr Asn Val Ser Asp
1               5                   10                  15

<210> SEQ ID NO 16
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Lys Ser Val His Ser Phe Asp Tyr Asp Trp Tyr Asn Val Ser Asp Gln
1               5                   10                  15

<210> SEQ ID NO 17
<211> LENGTH: 17
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Asn Lys Ser Val His Ser Phe Asp Tyr Asp Trp Tyr Asn Val Ser Asp
1               5                   10                  15

Gln

<210> SEQ ID NO 18
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Asn Lys Ser Val His Ser Phe Asp Tyr Asp Trp Tyr Asn Val Ser Asp
1               5                   10                  15

Gln Ala

<210> SEQ ID NO 19
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gln Asn Lys Ser Val His Ser Phe Asp Tyr Asp Trp Tyr Asn Val Ser
1               5                   10                  15

Asp Gln Ala

<210> SEQ ID NO 20
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gln Asn Lys Ser Val His Ser Phe Asp Tyr Asp Trp Tyr Asn Val Ser
1               5                   10                  15

Asp Gln Ala Asp
            20

<210> SEQ ID NO 21
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Ser Gln Asn Lys Ser Val His Ser Phe Asp Tyr Asp Trp Tyr Asn Val
1               5                   10                  15

Ser Asp Gln Ala Asp
            20
```

```
<210> SEQ ID NO 22
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Ser Gln Asn Lys Ser Val His Ser Phe Asp Tyr Asp Trp Tyr Asn Val
1               5                   10                  15

Ser Asp Gln Ala Asp Leu
            20

<210> SEQ ID NO 23
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Phe Ser Gln Asn Lys Ser Val His Ser Phe Asp Tyr Asp Trp Tyr Asn
1               5                   10                  15

Val Ser Asp Gln Ala Asp Leu
            20

<210> SEQ ID NO 24
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Phe Ser Gln Asn Lys Ser Val His Ser Phe Asp Tyr Asp Trp Tyr Asn
1               5                   10                  15

Val Ser Asp Gln Ala Asp Leu Lys
            20

<210> SEQ ID NO 25
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Ser Phe Ser Gln Asn Lys Ser Val His Ser Phe Asp Tyr Asp Trp Tyr
1               5                   10                  15

Asn Val Ser Asp Gln Ala Asp Leu Lys
            20                  25

<210> SEQ ID NO 26
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26
```

```
Cys Ser Phe Ser Gln Asn Lys Ser Val His Ser Phe Asp Tyr Asp Trp
1               5                  10                  15

Tyr Asn Val Ser Asp Gln Ala Asp Leu Lys Asn
                20                  25

<210> SEQ ID NO 27
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Cys Met Phe Ser Val Pro Phe Asp Tyr Cys
1               5                  10
```